United States Patent [19]

Chasar

[11] 4,163,008

[45] Jul. 31, 1979

[54] DUAL PURPOSE STABILIZER COMPOUNDS AND POLYMER COMPOSITIONS CONTAINING SAME

[75] Inventor: Dwight W. Chasar, Northfield, Ohio

[73] Assignee: The B. F. Goodrich Company, Akron, Ohio

[21] Appl. No.: 892,005

[22] Filed: Mar. 31, 1978

[51] Int. Cl.² .................... C08K 5/36; C07C 153/07
[52] U.S. Cl. ...................... 260/45.85 B; 260/455 R
[58] Field of Search ............... 260/45.85 B, 455 R

[56] References Cited

U.S. PATENT DOCUMENTS

| | | | |
|---|---|---|---|
| 3,598,854 | 8/1971 | Steinberg | 260/45.85 B |
| 3,636,033 | 1/1972 | Kleiner | 260/45.85 B |
| 3,657,309 | 4/1972 | Dexter et al. | 260/455 |
| 4,051,104 | 9/1977 | Spivack et al. | 260/455 |

FOREIGN PATENT DOCUMENTS 42-6332 3/1967 Japan ..................... 260/455

*Primary Examiner*—V. P. Hoke
*Attorney, Agent, or Firm*—John H. Faro

[57] ABSTRACT

Diesters of partially hindered mercaptophenols and 3,5-di-alkyl-4-hydroxybenzoic acid and its corresponding acid salt, wherein such diester corresponds to the following formula

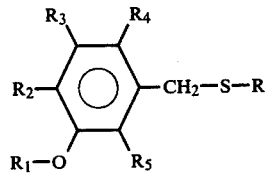

wherein R and $R_1$ are the same and are selected from among the following

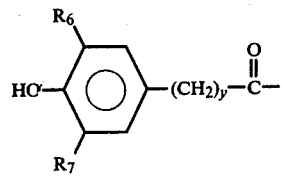

with $R_6$ and $R_7$ being an aliphatic hydrocarbon radical of 3 to 10 carbon atoms; and y being 0-5;

$R_2$ is a tertiary aliphatic hydrocarbon radical having from 4 to 10 carbon atoms or an alicyclic hydrocarbon radical having from 4 to 10 carbon atoms, where the carbon atom of attachment to the aromatic ring is fully substituted;

$R_3$ is hydrogen, halogen, an aliphatic hydrocarbon radical having from 1 to 10 carbon atoms or an alicyclic hydrocarbon radical having from 3 to 10 carbon atoms; and $R_4$ and $R_5$ is

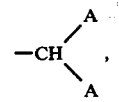

where where A and A' are independently selected from among hydrogen, an aliphatic hydrocarbon radical of 1 to 10 carbon atoms or an alicyclic hydrocarbon radical of 3 to 10 carbon atoms.

The above diesters are highly effective stabilizers of polyolefins against oxidative degradation and also impart a modest degree of protection and such materials against UV degradation.

6 Claims, No Drawings

DUAL PURPOSE STABILIZER COMPOUNDS AND POLYMER COMPOSITIONS CONTAINING SAME

BACKGROUND OF THE INVENTION

1. Field of the Invention

This invention is directed to novel compounds and polymeric compositions containing such novel compounds. More specifically, this invention concerns itself with a new class of stabilizer for polyolefins and stabilized polymeric materials which are resistant to oxidative degradation and possess enhanced stability even after prolonged exposure to ultraviolet light.

2. Description of the Prior Art

Polymers have in the past and continue to provide an attractive substitute for other more traditional types of structural materials (e.g. wood and metals) because of relatively inexpensive materials and fabrication costs. As polymers continue to find new applications in, for example, the fabrication of automotive parts and building materials, they must also become more durable and capable of withstanding prolonged exposure to a variety of degradative forces. Degradation of polymers can be caused by exposure to light, heat and/or air. Such degradation is usually manifest by either a partial or total loss of structural integrity, changes in light transmission properties, changes in color, loss or reduction in flexibility and/or resiliency, or any combination of the above phenomena. Those attempting to avoid polymer degradation have generally selected from among three possible approaches: (a) elimination or reduction of the degradative forces; (b) isolation of the sensitive polymer material from the degradative forces; or (c) modification of the polymer composition to enhance its resistance to the degradative forces. The latter approach is generally preferable since it does not require elaborate engineering or structural changes in the polymer product environment.

There are a variety of additives which have been disclosed as suitable for enhancing the resistance of polymers to one or more of the degradative forces discussed hereinabove. These additives (hereinafter referred to as "stabilizers") can be physically combined with or engrafted upon the environmentally sensitive polymer, thereby prolonging its useful life in the hostile degradative environment. Stabilizers are available which can enhance the polymer's resistance to one or more of the degradative forces discussed hereinabove and conversely, a stabilizer which is effective for prevention of, for example, oxidative degradation may have little if any effect upon the polymers resistance to other degradative agents. Thus, it is not uncommon for polymers to contain a variety of stabilizer materials, each being present for the prevention of a particular degradative reaction.

One of the more difficult to control of the degradative reactions results from exposure of the polymer to the oxygen present in the atmosphere. The impact of such exposure will, of course, vary upon temperature prevailing at the time of such exposure and the presence or absence of other agents either within the polymeric material or in contact with the polymeric material which can accelerate such degradation. Ordinarily, the effects of oxidation manifest themselves only after a prolonged interval and repeated exposure. The exposure of polymers to the degradative forces of oxidation can result in a variety of changes in such materials depending upon the degree of saturation of the polymer backbone and the various substituents pendant from the backbone. The oxidative degradation of polyolefins and dienic polymers is, however, mechanistically distinct, thus a stabilizer which is effective for prevention of oxidative degradation of polyolefins will in all likelihood be ineffective to impart similar protection to dienic polymers.

A number of materials are presently commercially available which are highly effective in the stabilization of polyolefins against oxidative degradation. Among the more prominently mentioned are Goodrite 3125 (a triester of a substituted cinnamic acid and 1,3,5-tris[2-hydroxyethyl]-s-triazine-2,4,6 trione, available from The B.F. Goodrich Company) and Plastinox 1729 (a diester of a partially hindered mercaptophenol and 1,4-benzenedicarboxylic acid, availabe from American Cyanamid Company). As is true of all additives to polymeric materials, stabilizing agents must be compatible with the host resin and have a minimum of impact upon the processing characteristics of the resin when present therein at concentrations necessary to impart the desired stabilizing characteristic. In addition, such additives and stabilizers should not change the color characteristics, clarity, or other aesthetic properties of the resin in which they are used. As will be appreciated, the latter requirements are only of importance where the stabilized polymer composition is used in the environment where retention of its original appearance is important.

In addition to its compatibility in the host polymer resin, stabilizers must be effective at relatively low concentrations and remain relatively immobile within the stabilized composition during the useful lifetime of the polymeric material. Where stabilizers are free to migrate within the polymer or are volatile at relatively low temperatures, such mobility can result in anisotropic redistribution of the stabilizer within the host polymer or the total loss of the stabilizer from the polymer. In either event, portions of the polymer will be rendered vulnerable to attack by degradative agents and thus the effectiveness of the stabilizer lost.

As is apparent from the above discussion, polymer stabilization against oxidative degradation has been and continues to present serious problems. Although there are a number of materials which are both effective and commercially available to stabilize the polymers against the degradative action of oxygen in the surrounding environment, such agents may, for one reason or another, be incompatible with other compounding ingredients or lack the chemical stability required of such materials (this latter criteria being critical where aesthetic appearance is important).

Thus, there is a continuing need for antioxidants which are both effective for preventing oxidative degradation of polymeric materials and yet compatible with processing and end use requirements of the resin.

SUMMARY OF THE INVENTION

Accordingly, it is the object of this invention to remedy the above as well as related deficiencies in the prior art.

More specifically, it is the principal object of this invention to provide a novel class of compounds which are effective in the stabilization of polymeric materials against oxidative degradation.

It is another object of this invention to provide a novel class of materials which are effective for the stabilization of polymeric materials against the degradative forces of both oxygen and ultraviolet light.

It is yet another object of this invention to provide a novel class of stabilizer material which is effective for stabilization of polymeric materials against the forces of oxidative and UV degradation while at the same time achieving such beneficial results without altering the aesthetic properties of the stabilized polymeric material.

Additional objects of this invention include providing stabilized polymer composition and a method for the stabilization of polymer compositions so as to extend their useful life in a degradative environment.

SUMMARY OF THE INVENTION

The above and related objects are achieved by providing a novel class of stabilizer compounds which comprise diesters of a partially hindered mercaptophenol and 3,5-di-alkyl-4-hydroxybenzoic acid, or its corresponding acid salt, wherein such diester corresponds to the following formula:

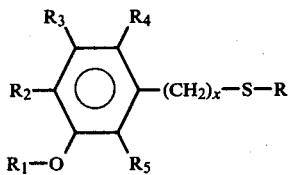

wherein
R and $R_1$ are the same and are selected from among the following

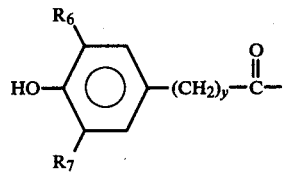

with
$R_6$ and $R_7$ being an aliphatic hydrocarbon radical of 3 to 10 carbon atoms; and y being 0–5;
$R_2$ is a tertiary aliphatic hydrocarbon radical having from 4 to 10 carbon atoms or an alicyclic hydrocarbon radical having from 4 to 10 carbon atoms, where the carbon atom of attachment to the aromatic ring is fully substituted;
$R_3$ is hydrogen, halogen, an aliphatic hydrocarbon radical having from 1 to 10 carbon atoms or an alicyclic hydrocarbon radical having from 3 to 10 carbon atoms; and
$R_4$ and $R_5$ is

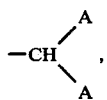

where
A and A' are independently selected from among hydrogen, an aliphatic hydrocarbon radical of 1 to 10 carbon atoms or an alicyclic hydrocarbon radical of 3 to 10 carbon atoms.

The above stabilizer compounds are highly effective in extending the useful life of polyolefins against degradation by oxygen present in the environment and Virtually all polymeric materials are sensitive, at least to some degree to oxidative degradation and to photoinduced degradation by ultraviolet light. The terms "oxidative degradation" and "photodegradation" are used throughout this disclosure, in reference to the environmentally sensitive polymers, to describe any oxidative changes and photo-induced changes in the physical, chemical and/or electrical properties induced in the polymer upon exposure of the polymer to such degradative forces. Such degradative changes in the polymer can include crosslinking, dehydrohalogenation, reduction in chain length, photooxidation, etc.

Polymers which are especially sensitive to oxidative degradation and photodegradation are materials which contain unsaturation along their respective backbone, vinyl halides polymers, polyolefins, polyacidaldehydes, ABS resins, polystyrene, polyacrylonitrile, polycarbonates, polyacrylates, poly-α-substituted acrylates, varnish, phenolformaldehyde resins, polyepoxides, polyester, and their respective blends and copolymers. The preferred environmentally sensitive polymer of the compositions of this invention are the poly-α-monoolefins. The α-monoolefin monomers from which the latter polymers can be derived, include ethylene, propylene, isobutylene, 1-butene, 1-pentene, 1-hexene, 4-methyl-1-pentene, and the like. The dual functional stabilizer described hereinabove is especially suitable for use in extending the useful lifetime of poly(propylene) in a hostile degradative environment.

The stabilized polymer compositions of this invention can contain, in addition to the dual functional stabilizer described hereinabove, a variety of optional ingredients. Such ingredients can include metal oxides, such as zinc, calcium and magnesium oxide, fatty acids, such as stearic, lauric and metal salts thereof; fillers, such as calcium and magnesium carbonate, calcium and barium, sulphonates, aluminum silicates, asbestos and the like; plasticizers and extenders, such as dialkyl and diaryl organic acids, such as diisobutyl, diisooctyl, diisodecyl and dibenzooleates, stearates, sebacates, azelates, phthalates, and the like; ASTM type II petroleum oils, paraffinic oils, castor oil, tall oil, glycerine anolyte; antioxidants, such as 2,6-di-t-butylparacresol, 2,2'-methylene-bis-(4-ethyl-6-t-butylphenol), 2,2'-thiobis(4-methyl-6-t-butylphenol), 2,2'-methylene-bis-(6-t-butyl-4-methylphenol), 4,4'-butylidene-bis(6-t-butyl-m-cresol), 2-(4-hydroxy-3,5-di-t-butylanilino-4,6-bis (octylthio) 1,3,5-triazine,hexahydro-1,3,5-tris-β-(3,5-di-t-butyl-4-hydroxyphenylpropionyl-s-triazine, tris-(3,5-di-t-butyl-4-hydroxybenzyl) isocyanurate, tetrakismethylene-3(3',5'-di-t-butyl-4'-hydroxyphenyl) propionate methane, distearylthiodipropionate, dilaurylthiodipropionate, tri(nonylphenyl)phosphite, tinthioglycolate, and the like; and other conventional ingredients such as pigments, tackifiers, flame retardants, fungicides and the like.

The stabilized polymer compositions of this invention can also include additional antioxidants; however, the effectiveness of the dual function stabilizers of this invention renders their addition unnecessary unless of course, the polymer composition were intended to be used in an ozone-rich environment. It thus may be desirable to include within the composition antioxidants which are especially adapted for combatting oxidative degradation which can be occasioned upon exposure to ozone. In such instances, the antiozonant can be present within the polymer composition within a range of concentration from about 0.1 to about 10 parts by weight per 100 parts by weight polymer, and preferably from about 0.2 to about 5 parts by weight per 100 parts by weight polymer. Generally, the phenolic antioxidants are also suitable for use in combatting the degradative forces of ozone.

Ordinarily, the environmentally sensitive polymer and the various types of stabilizers will be compounded with one another in accord with standard mixing techniques and equipment; such as, in a Banbury mixer, a Henschel mixer, a rubber mill, an extruder mixer or other equivalent device. The various components of the composition may be physically intimately blended either in the absence or in the presence of a common solvent; or in a solvent which is capable of dissolving the polymer components of the composition yet substantially incapable of dissolving the stabilizer ingredients. Typical of such solvent/dispersing agents include hexane or benzene. Subsequent to intimately dispersing the various components of the composition within one another, the dispersing agent (if any) can be removed therefrom by selective evaporation and the resultant resin recovered. The resin may thereafter be formed into usable products by a variety of standard molding techniques.

The efficacy of the dual purpose stabilizers of this invention is evaluated in the following manner: The antioxidant capabilities of the stabilizer are determined by preparation of a series of plaques from an environmentally sensitive polyolefin, such as polypropylene, and a novel dual purpose stabilizer. The concentration of stabilizer in the sample will be in the range of that normally used in commercial applications. The plaques prepared in this manner will be mounted on a glass rod and suspended in a draft oven operated at 140° C. Each plaque will be separated from one another by an appropriate spacer. The sample is deemed to have oxidized when any portion of the plaque becomes brittle or appears burnt. Oftentimes the sample may turn white and then appear scorched.

The ultraviolet light stability of the compositions of this invention is evaluated by exposing a film sample of a stabilized polymer composition to an Xenon or carbon arc light in a Weather-Ometer operated at a temperature of about 60° C. Degradation of the sample is monitored periodically by removal of the sample and measuring its infra-red spectrum from 1910 through 1700 $cm^1$. The development of carbonyl functionality at 1719 $cm^{-1}$ relative to the reference peak at 1890 $cm^{-1}$ (plotted against time) is monitored. The failure time is that period necessary for the carbonyl index to reach approximately 0.35 or brittleness, whichever occurs first. This test procedure is an accepted method for evaluation of UV stabilizers and is fully described in the open literature, see "*Photodegradation, Photooxidation and Photostabilization of Polymers*" by Ranby and Raybeck, John Wiley & Sons, New York City (1975) at page 125 et seq., and is also disclosed in U.S. Pat. No. 3,909,493. Photodegradation of the sample can also be visually manifested by cracking of the sample when it is heated to about 180° C.

The Examples which follow, further define, describe and illustrate the preparation and evaluation of the stabilizers and the stabilized compositions of this invention. Apparatus and procedures used in both the preparation and evaluation of such materials are standard, or as hereinbefore described. Parts and percentages appearing in such Examples are by weight unless otherwise stipulated.

EXAMPLE I 2,4-Dimethyl-6-t-butylphenol.

To a 1 liter flask equipped with a condenser, overhead stirrer, and gas inlet tube was added 2,4-dimethylphenol (200 g, 1.64 m.), toluene (400 ml), and p-toluenesulfonic acid (10 g). After heating this solution to reflux, isobutylene was added continuously for 14 hrs. Upon cooling, the solution was washed twice with water (400 ml), dried ($MgSO_4$), and the solvent evaporated to afford a dark brown liquid. GC confirmed that this liquid was about 72% product. Distillation afforded 253 g (86.6%) of clear product which was shown to be 97% pure by GC.

EXAMPLE II 2,4-Dimethyl-3-chloromethyl-6-t-butylphenol.

This material was prepared according to the procedure of Wegler and Regel (Wegler, R. and Regel, E., Makromol. Chem., 9, 1(1952)) using 2,4-dimethyl-6-t-butyl-phenol (65.0 g, 0.36 m), methylol (55 g, 0.72 m), sulfuric acid (7.22 ml), and concentrated hydrochloric acid (505 ml). Work-up by extraction with ether afforded a dark oil, whose ir and nmr spectra were consistent with the desired material.

EXAMPLE III 2,4-Dimethyl-3-mercaptomethyl-6-t-butylphenol.

This material was synthesized according to the procedure of Song (Song, J. U.S. Pat. No. 3,810,929) using 2,4-dimethyl-3-chloromethyl-6-t-butylphenol (160.8 g, 0.71 m), triethylamine (80 g), tetrahydrofuran (200 ml) and excess hydrogen sulfide. This afforded upon work-up a slightly yellow odorous oil.

EXAMPLE IV 2,4-Dimethyl-3-(2-hydroxyethylthiomethyl)-6-t-butylphenol.

This material was prepared according to the procedure of Example III using 2,4-dimethyl-3-chloromethyl-6-t-butylphenol (160.8 g, 0.71 m), 2-mercaptoethanol (52.5 g, 0.71 m), potassium carbonate (110.4 g, 0.8 m), potassium iodide (5.0 g), and methyl isobutyl ketone (500 ml). Work-up afforded a dark colored oil. This material can be distilled under a very good vacuum. The nmr spectrum was consistent with the desired structure.

EXAMPLE V 3,5-Di-t-butyl-4-hydroxybenzoyl chloride.

To a 3-necked flask equipped with a magnetic stirrer, thermometer, and water condenser with a drying tube is added 3,5-di-t-butyl-4-hydroxybenzoic acid (12.5 g, 0.05 m), thionyl chloride (10 ml) and 5 drops of pyridine. This mixture is heated at 45° C. for 1.5 hr. After cooling to RT, 50 ml of benzene is added. After stirring for 15 min., the benzene is evaporated under water aspirator vacuum leaving a yellow solid. This is dissolved in petroleum ether (at 35°–55° C.), filtered, and evaporated to afford 11 g of a yellow solid, mp 90°–93° (lit.mp. 96°–99°).

EXAMPLE VI 2,6-Dimethyl-4-t-butyl-3-(3,5-di-t-butyl-4-hydroxy benzoyloxy)benzyl 3,5-di-t-butyl-4-hydroxythiobenzoate.

A solution of 2,4-dimethyl-3-mercaptomethyl-6-t-butylphenol (26.38 g, 0.12 m), 3,5-di-t-butyl-4-hydroxybenzoyl chloride (31.0 g, 0.12 m), triethylamine (11.67 g, 0.12 m), and benzene (250 ml) was stirred at RT for 24 hrs. The mixture was washed with 1 N HCl, water, dried ($Na_2SO_4$), and the solvent evaporated to afford a thick dark yellow oil. This was dissolved in hexane, cooled for 24 hours, and filtered to afford 14.8 g of a white microcrystalline sold, mp. 225°–228° C. The ir and nmr were consistent with the desired structure. Anal. Calcd. for $C_{43}H_{60}O_5S$:C, 74.96; H, 8.78; S, 4.65 Found: C, 74.64; H, 8.79; S, 4.93.

EXAMPLE VII 2,6-Dimethyl-3-hydroxy-4-t-butylbenzyl 3,5-di-t-butyl-4-hydroxythiobenzoate.

A solution of 2,4-dimethyl-3-mercaptomethyl-6-t-butylphenol (4.48 g, 0.02 m), 3,5-di-t-butyl-4-hydroxybenzoyl chloride (5.38 g, 0.02 m), triethylamine (2.40 g, 0.024 m) and benzene (50 ml) was stirred overnight at RT. The mixture was washed with 1 N HCl, water, dried ($Na_2SO_4$), and the solvent removed to afford a thick yellow syrup. This was column chromatographed on Woelm silica gel (160 g) using 1:2 hexane-benzene as the eluent affording less than a gram of an off-white solid, whose nmr spectrum indicated it to be primarily the desired material.

EXAMPLE VIII 2-(2,6-Dimethyl-3-hydroxy-4-t-butylbenzylthio) ethyl 3,5-di-t-butyl-4hydroxybenzoate.

A solution of 2,4-dimethyl-3-(2-hydroxyethylthiomethyl) 6-t-butylphenol (2.68 g, 0.01 m), 3,5-di-t-butyl-4-hydroxybenzoyl chloride (2.69 g, 0.01 m), pyridine (1.0 g, 0.013 m), and benzene (30 ml) was stirred four 4 hr. at 42° C. After filtering the mixture, the filtrate was washed with 1 N HCl and water, dried ($Na_2SO_4$), and the solvent removed to yield a viscous yellow oil. This was column chromatographed on 160 g of Woelm silica gel using benzene as the eluent, affording a white solid, which still contained impurities by tlc. The nmr spectrum, however, was consistent with the desired structure.

EXAMPLE IX 2-(2,6-Dimethyl-3-hydroxy-4-t-butylbenzylthio)ethyl 3-(3,5-di-t-butyl-4-hydroxyphenyl)propionate.

To a flask equipped with a heating mantle, magnetic stirrer, and a dry-ice trap was added 2,4-dimethyl-3-(2-hydroxyethylthiomethyl)-6-t-butylphenol (10.72 g, 0.04 m) and ethyl 3-(3,5-di-t-butyl-4-hydroxyphenyl) propionate (12.24 g, 0.04 m). The contents of the flask was heated to 140° C. and subjected to a 40 mm Hg partial vacuum. Five drops of tetraisopropyl titanate were added and immediately a clear liquid collected in the dry-ice trap. The temperature was raised to 180° C. and held there for one hr. Five more drops of catalyst were added and the conditions continued for one hr. more. The reaction was then stopped.

The dark viscous oil remaining in the flask was column chromatographed on 400 g of silica gel (Fisher Brand, 28-200 mesh) using benzene as the eluent, giving 10 g of still impure product. This was rechromatographed on 165 g of Woelm silica gel using benzene as the eluent, affording about 1.6 g of fairly pure tan product, mp 96°–103° C. The ir and nmr spectra were consistent with the desired structure.

EXAMPLE X

Benzyl 3,5-di-t-butyl-4-hydroxythiobenzoate.

3,5-Di-t-butyl-4-hydroxybenzoyl chloride (12.5 g, 0.047 m) in benzene (50 ml) was rapidly added to a solution of α-toluenethiol (5.78 g, 0.047 m) and triethylamine (4.71 g, 0.047 m) in 150 ml of benzene at RT. This was stirred for one hour. The mixture was washed with 2 N NaOH (100 ml) and water (2×100 ml), the organic layer dried ($MgSO_4$) and evaporated to afford a yellow oil. This was triturated with a small amount of hexane, cooled, and filtered to afford 4.0 g (24%) of a white solid, mp 115°–119° C. The ir and nmr spectra were consistent with the desired structure.

Table I contains oven aging data for polypropylene films stabilized with both mono and diesters of partially hindered mercaptophenols and 3,5-di-alkyl-4-hydroxybenzoic acid (or its corresponding acid salt), and a variety of other compounds (some of which are commercially available). The concentration of compound in the film is given in parts per 100 parts by weight of resin (phr).

TABLE 1

| Antioxidant | Conc. (phr) | Time to Failure in 140° Oven-aging (Days) |
|---|---|---|
| (Diester of Example VI) | 0.10 | 14 |
|  | 0.25 | 48 |
|  | 0.50 | 66 |

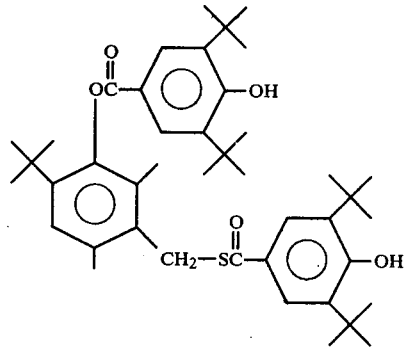

TABLE 1-continued

| Antioxidant | Conc. (phr) | Time to Failure in 140° Oven-aging (Days) |
| --- | --- | --- |
| (hindered phenol-CH₂-S-C(=O)-phenol-hindered) | 0.10 | 2 |
|  | 0.25 | 4 |
| (hindered phenol-CH₂SCH₂CH₂OC(=O)-phenol-hindered) | 0.10 | 1⅜ |
|  | 0.25 | 3 |
| (hindered phenol-CH₂SCH₂CH₂OC(=O)CH₂CH₂-phenol-hindered) | 0.10 | 5 |
|  | 0.25 | 11 |

TABLE 2

| Compound | Conc. (phr) | Oven-aging Days to Failure 140° C. | Oven-aging Days to Failure 150° C. | Xenon Weather-Ometer Hours To Failure |
| --- | --- | --- | --- | --- |
| Diester | 0.10 | 14 | 2¼ | 875 |
|  | 0.25 | 48 | 11⅜ | 1120 |
|  | 0.50 | 66 | 21¼ | 1350 |
| Goodrite 3125 | 0.10 | 42 | 5⅜ |  |
|  | 0.25 | 51 | 20⅜ | 560 |
|  | 0.50 | 11 | 29⅜ |  |
| Goodrite 3114 | 0.10 | 6 | 1⅜ |  |
|  | 0.25 | 6 | 2¼ | 1040 |
|  | 0.50 | 42 | 4⅞ |  |
| BHT | 0.10 | 1 | 1 |  |
|  | 0.25 | 1 | 1 | 1138 |
|  | 0.50 | 1 | 1 |  |
| Plastinox 1729 | 0.10 | 29 | 6⅛ |  |
|  | 0.25 | 51 | 14¼ | 400 |
|  | 0.50 | 58 | 19⅜ |  |
| AM 340 | 0.25 | 1 |  | 3000 |
| Tinuvin 327 | 0.25 | 1 |  | 700-1200 |
| Control | — | 1 |  | 500 |

Table 2 provides comparative data of the UV stabilization of polypropylene film with the diester of this invention and with commercially available stabilizers. Also reproduced on Table 2 is the over aging data of Table 1 (at 140° C.) and additional aging data at 150° C. This side-by-side comparison readily demonstrates the dual stabilization capabilities of the compounds of the instant invention.

As is evident from Table I, the model compound (the diester) is significantly more effective as an antioxidant than the intermediate from which the diester is prepared. In addition, the diester is significantly more effective than the other two monoesters shown notwithstanding the presence of both hindered and less hindered phenolic groups pendant from the respective ends of each compound.

The data presented in Table 2 clearly demonstrates that the diester is a better antioxidant than Plastinox 1729 at the higher concentrations tested. The diester also is comparable to Goodrite 3114 in UV stabilization. In no instances do any of the compounds evaluated compare favorably with the diester in both areas of stabilization. This fact enables the use of reduced concentrations of additives to polymers, thereby enabling significant cost savings, and minimizing impairment in the polymer properties during both processing and in end use.

Table 3 which follows provides comparative data for stabilizer formulations containing the diester.

TABLE 3

| Diester Conc. | Conc./Commercial Stabilizer | Days to Failure+ 140° Oven-aging | Hours to Failure Weather-Ometer |
| --- | --- | --- | --- |
| 0.10 | — | 14 | 875 |
| 0.25 | — | 48 | 1120 |
| 0.50 | — | 66 | 1350 |
| — | 0.25 Goodrite 3114 | 5 | 1040 |
| 0.10 | 0.25 Goodrite 3114 | 28 (19) | 875 |
| 0.25 | 0.25 Goodrite 3114 | 67 (53) | 1050 |
| 0.50 | 0.25 Goodrite 3114 | 82 (71) | 875 |
| 0.25 | 0.10 Goodrite 3114 | 60 (53) | 1190 |
| 0.25 | 0.25 Goodrite 3114 | 67 (53) | 1050 |
| 0.25 | 0.50 Goodrite 3114 | 84 (90) | 875 |
| — | 0.25 DSTDP | <3 |  |

TABLE 3-continued

| Diester Conc. | Conc./Commercial Stabilizer | Days to Failure+ 140° Oven-aging | Hours to Failure Weather-Ometer |
|---|---|---|---|
| 0.10 | 0.25 DSTDP | 52 (17) | |
| 0.25 | 0.25 DSTDP | 67 (51) | |
| 0.50 | 0.25 DSTDP | 83 (69) | |
| — | 0.25 Weston 618 | 1 | |
| 0.10 | 0.25 Weston 618 | 8 (15) | |
| 0.25 | 0.25 Weston 618 | 75 (49) | |
| 0.50 | 0.25 Weston 618 | 56 (67) | |
| 0.25 | 0.25 Irganox 1010 | 67 | 974 |

+The numbers in ( ) represent the sum of the failure times of each of the individual components.

As evident from Table 3, a diester of this invention is highly compatible with a number of other commercially available stabilizers.

The foregoing Examples clearly demonstrate the dual functional stabilization capabilities of the compounds of this invention when used in conjunction with environmentally sensitive polymers, such as polypropylene. The foregoing description and Examples have been provided for the purposes of illustration of some of the preferred embodiments of this invention and not intended to delineate its scope which is set forth in the following claims.

What is claimed is:

1. Compounds of the formula

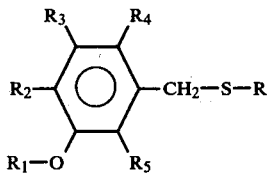

wherein

R and R1 are the same and are selected from among the following

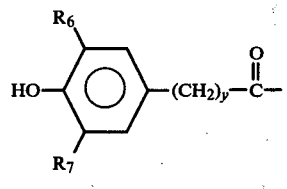

with $R_6$ and $R_7$ being an aliphatic hydrocarbon radical of 3 to 10 carbon atoms; and y being 0-5;

$R_2$ l is a tertiary aliphatic hydrocarbon radical having from 4 to 10 carbon atoms or an alicyclic hydrocarbon radical having from 4 to 10 carbon atoms, where the carbon atom of attachment to the aromatic ring is fully substituted;

$R_3$ is hydrogen, halogen, an aliphatic hydrocarbon radical having from 1 to 10 carbon atoms or an alicyclic hydrocarbon radical having from 3 to 10 carbon atoms; and $R_4$ and $R_5$ is

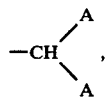

where

A and A' are independently selected from among hydrogen, an aliphatic hydrocarbon radical of 1 to 10 carbon atoms or an alicyclic hydrocarbon radical of 3 to 10 carbon atoms.

2. The compound of claim 1, 2,6-dimethyl-4-t-butyl-3-(3,5-di-t-butyl-4-hydroxy-benzoyloxy)benzyl 3,5-di-t-butyl-4-hydroxythiobenzoate.

3. A composition comprising a polymer which is sensitive to oxidative degradation and an antioxidant effective amount of at least one compound of the formula

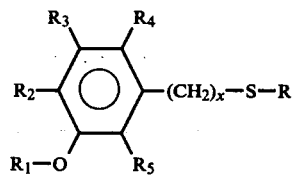

wherein

R and $R_1$ are the same and are selected from among the following

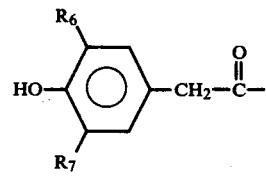

with $R_6$ and $R_7$ being an aliphatic hydrocarbon radical of 3 to 10 carbon atoms; and y being 0-5;

$R_2$ is a tertiary aliphatic hydrocarbon radical having from 4 to 10 carbon atoms or an alicyclic hydrocarbon radical having from 4 to 10 carbon atoms, where the carbon atom of attachment to the aromatic ring is fully substituted;

$R_3$ is hydrogen, halogen, an aliphatic hydrocarbon radical having from 1 to 10 carbon atoms or an alicyclic hydrocarbon radical having from 3 to 10 carbon atoms; and $R_4$ and $R_5$ is

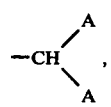

where

A and A' are independently selected from among hydrogen, an aliphatic hydrocarbon radical of 1 to 10 carbon atoms or an alicyclic hydrocarbon radical of 3 to 10 carbon atoms.

4. The composition of claim 3, wherein the compound is 2,6-dimethyl-4-t-butyl-3-(3,5-di-t-butyl-4-hydroxy-benzoyloxy)benzyl 3,5-di-t-butyl-5-hydroxy-thiobenzoate.

5. A composition comprising a polymer which is sensitive to UV degradation and a UV stabilization effective amount of at least 1 compounds of the formula

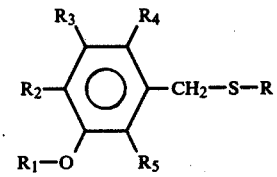

wherein

R and $R_1$ are the same and are selected from among the following

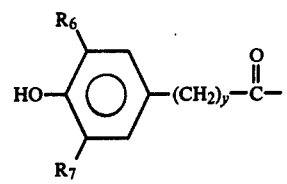

with $R_6$ and $R_7$ being an aliphatic hydrocarbon radical of 3 to 10 carbon atoms; and y being 0–5;

$R_2$ is a tertiary aliphatic hydrocarbon radical having from 4 to 10 carbon atoms or an alicyclic hydrocarbon radical having from 4 to 10 carbon atoms, where the carbon atom of attachment to the aromatic ring is fully substituted;

$R_3$ is hydrogen, halogen, an aliphatic hydrocarbon radical having from 1 to 10 carbon atoms or an alicyclic hydrocarbon radical having from 3 to 10 carbon atoms; and $R_4$ and $R_5$ is

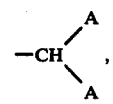

where

A and A' are independently selected from among hydrogen, an aliphatic hydrocarbon radical of 1 to 10 carbon atoms or an alicyclic hydrocarbon radical of 3 to 10 carbon atoms.

6. The composition of claim 5, wherein the compound is 2,6-dimethyl-4-t-butyl-3-(3,5-di-t-butyl-4-hydroxy-benzoyloxy)benzyl 3,5-di-t-butyl-4-hydroxy-thiobenzoate.

* * * * *

UNITED STATES PATENT AND TRADEMARK OFFICE
CERTIFICATE OF CORRECTION

PATENT NO. : 4,163,008

DATED : July 31, 1979

INVENTOR(S) : Dwight W. Chasar

It is certified that error appears in the above-identified patent and that said Letters Patent are hereby corrected as shown below:

In the Claim 3, the formula appearing at lines 26-34 should be changed to read as follows:

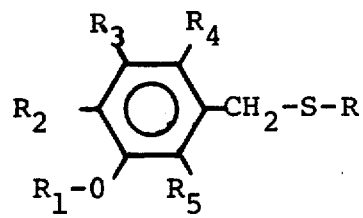

UNITED STATES PATENT AND TRADEMARK OFFICE
CERTIFICATE OF CORRECTION

PATENT NO. : 4,163,008
DATED : July 31, 1979
INVENTOR(S) : Dwight W. Chasar

It is certified that error appears in the above-identified patent and that said Letters Patent are hereby corrected as shown below:

In the Claim 3, the formula appearing at lines 38-46 should be changed to read as follows:

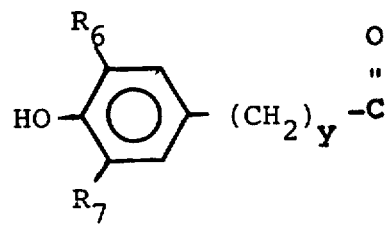

Signed and Sealed this

First Day of January 1980

[SEAL]

Attest:

SIDNEY A. DIAMOND

*Attesting Officer*  *Commissioner of Patents and Trademarks*